(12) United States Patent
Harris

(10) Patent No.: US 7,028,956 B2
(45) Date of Patent: Apr. 18, 2006

(54) TWO-PIECE SURGICAL CORD HOLDER

(76) Inventor: Jonathan Harris, 23 Country La., Vernon, VT (US) 05354

( * ) Notice: Subject to any disclaimer, the term of this patent is extended or adjusted under 35 U.S.C. 154(b) by 70 days.

(21) Appl. No.: 10/943,243

(22) Filed: Sep. 16, 2004

(65) Prior Publication Data

US 2006/0054747 A1    Mar. 16, 2006

(51) Int. Cl.
*F16L 3/08*        (2006.01)
(52) U.S. Cl. .................. 248/65; 248/227.1; 248/228.1; 248/226.11; 248/231.85; 248/229.2; 248/229.15
(58) Field of Classification Search .................. 248/65, 248/227.2, 228.1, 226.11, 227.1, 231.85, 248/229.2, 229.15, 300, 301, 303, 306, 316.1
See application file for complete search history.

(56) References Cited

U.S. PATENT DOCUMENTS

| | | | |
|---|---|---|---|
| 1,335,308 A * | 3/1920 | Wilson | 248/316.1 |
| 2,843,196 A * | 7/1958 | Schauer | 297/188.03 |
| 2,885,696 A * | 5/1959 | Sauer, Jr. | 114/364 |
| 3,317,171 A * | 5/1967 | Kramer | 248/229.15 |
| D305,299 S * | 1/1990 | Freeman | D8/373 |
| 5,044,589 A * | 9/1991 | Milne et al. | 248/265 |
| 5,141,185 A * | 8/1992 | Rumbold et al. | 248/71 |
| 6,375,132 B1 * | 4/2002 | Tomlinson | 248/117.6 |

* cited by examiner

*Primary Examiner*—Robert P. Olszewski
*Assistant Examiner*—Todd M. Epps
(74) *Attorney, Agent, or Firm*—John J. Welch, Jr., Esq.

(57) ABSTRACT

The invention is a two-piece surgical cord holder with the first unit thereof being in the shape of nearly a right angle with the other unit thereof thereof polysided with three horizontally inclined sides, three vertically inclined sides, a plurality of threaded through holes in the first of the vertically inclined sides for receipt through one of them and a through hole in either leg of the first unit of a first turning screw component serving to hold the fully assembled cord holder fast to the lateral side of a tabletop portion of a surgical operating table and a threaded hole in the first of the three horizontally inclined sides for receipt of a second turning screw component serving to hold the fully assembled cord holder fast to the bottom side of the tabletop portion of the table.

6 Claims, 5 Drawing Sheets

TWO-PIECE SURGICAL CORD HOLDER

CROSS REFERENCES TO PRIOR OR PARENT APPLICATIONS

There are no prior or parent applications to which the instant invention relates.

FEDERALLY SPONSORED RESEARCH AND DEVELOPMENT

The instant invention has not been the subject of any federally sponsored research and development.

BACKGROUND OF THE INVENTION

1. Field of the Invention

The instant invention is one of that category of devices that serve to promote greater efficiency in the performance of surgical procedures.

2. Informational Art Statement

The devices which are enumerated in the Informational Art Statement which is herewith submitted may resemble but do not anticipate the instant invention.

A SUMMARY OF THE INVENTION

1. A Brief Description of the Invention:

The invention is a two-piece surgical cord holding device that is affixable to one of the lateral sides of the tabletop portion of a surgical operating table. The first piece thereof is a first connecting unit in the shape of roughly a right angle gently curved at the apex thereof with a through hole in each leg thereof. The second piece thereof is a second connecting unit that is polysided. It has a first vertically inclined side extended downwardly, gently curving at an end thereof into a first horizontally inclined side that gently curves into a downwardly directed second vertically inclined side gently curving at an end thereof into a second horizontally inclined side directed opposite to the direction taken by the first horizontally inclined side. The outer end of the second horizontally inclined side which is shorter in length than the first gently curves into an upwardly directed third vertically inclined side that in turn, at its uppermost end gently curves into a third horizontally inclined side shorter in length than the second and directed opposite to the direction taken by the second horizontally inclined side. One of a pair of threaded through holes in the first vertically inclined side receives, through one of the through holes in the first connecting unit, a first turning screw component that serves to hold the two connecting units together as well as to hold the fully assembled invention fast to the above specified side of the tabletop portion of the surgical table. A threaded through hole in the first horizontally inclined side serves to receive a second turning screw component that serves to hold the assembled invention fast to the bottom side of the table top of the surgical operating table.

2. Objects of the Invention:

One of the major difficulties encountered by operating room personnel is the one where one or more of them are constantly having to step around surgical cords lying about the floor. These are cords that run from electrical outlets to, for example, electrically energized thermal blankets attached to a surgical operating table or such cording attached to i.e., an electrically served compression device serving to prevent blood clotting when applied to the limbs of a patient undergoing surgery. There is also a similar problem encountered with respect to cables on the floor of every operating room that serve to energize, for example, foot pedal controls designed to facilitate variation of positioning of attached component parts of a surgical tabletop holding a patient during surgery. One can only imagine how serious a problem there could be, if during the course of an extremely delicate and intricate part of a serious surgical procedure, the surgeon found himself or herself suffering a tripping incident over and upon one or more pieces of cording or cable under his or her feet. There is also a problem with such cords and/or cables getting caught under the surgical table. The instant invention serves to completely obviate these problems by way of causing such cording and cables in the vicinity of the operating table to be held above floor level.

In view of the foregoing, respectfully submitted, the instant invention is indeed new, useful and unique.

A BRIEF DESCRIPTION OF THE DRAWINGS

A DESCRIPTION OF THE PREFERRED EMBODIMENTS

Figure 1:
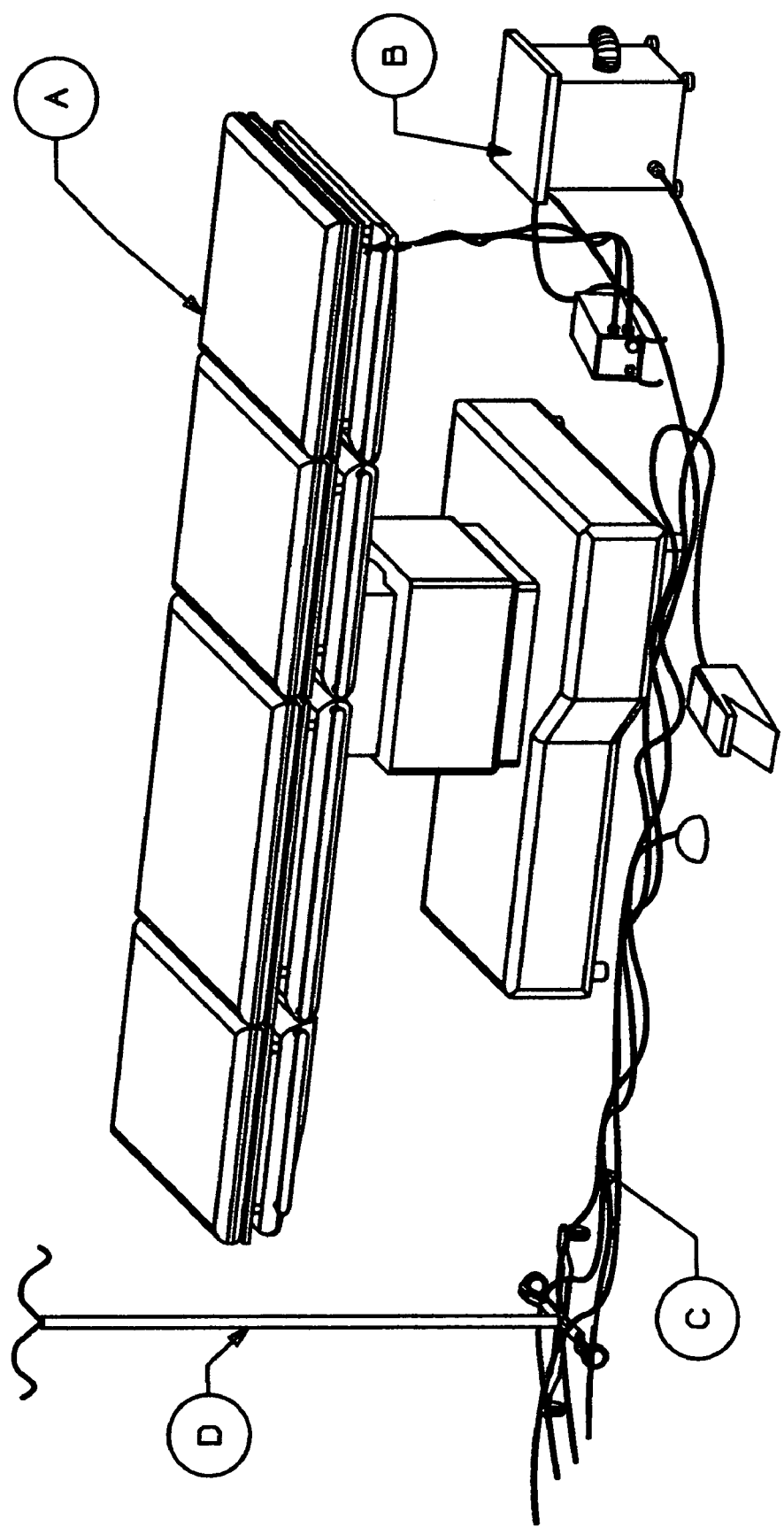
FIG. 1 shows an operating table with various cords and cables on the floor thereabouts.
Figure 2:
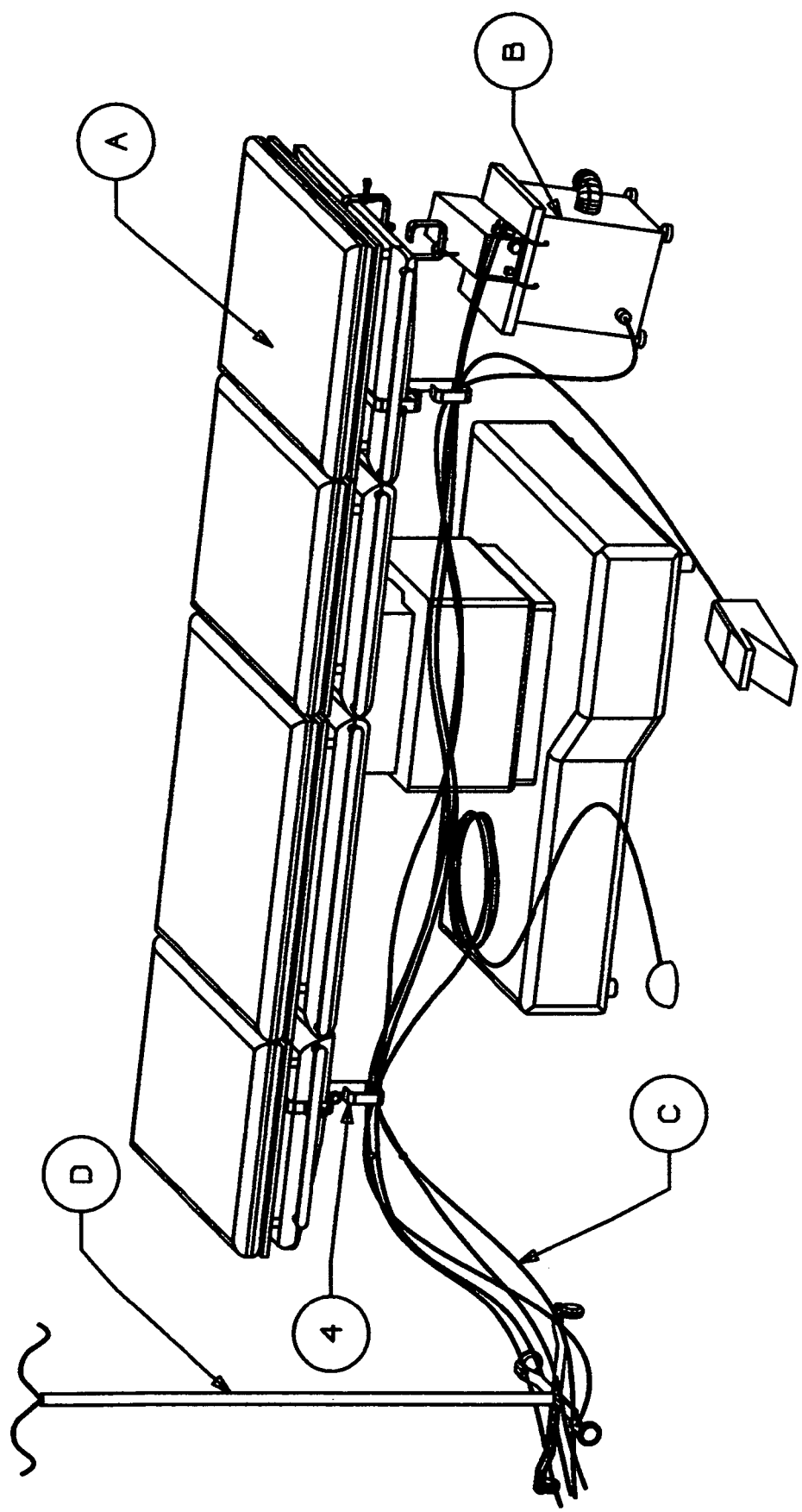
FIG. 2 shows the same operating table, cords and cables as seen in FIG. 1 however equipped with a plurality of units of the instant invention.
Figure 3:
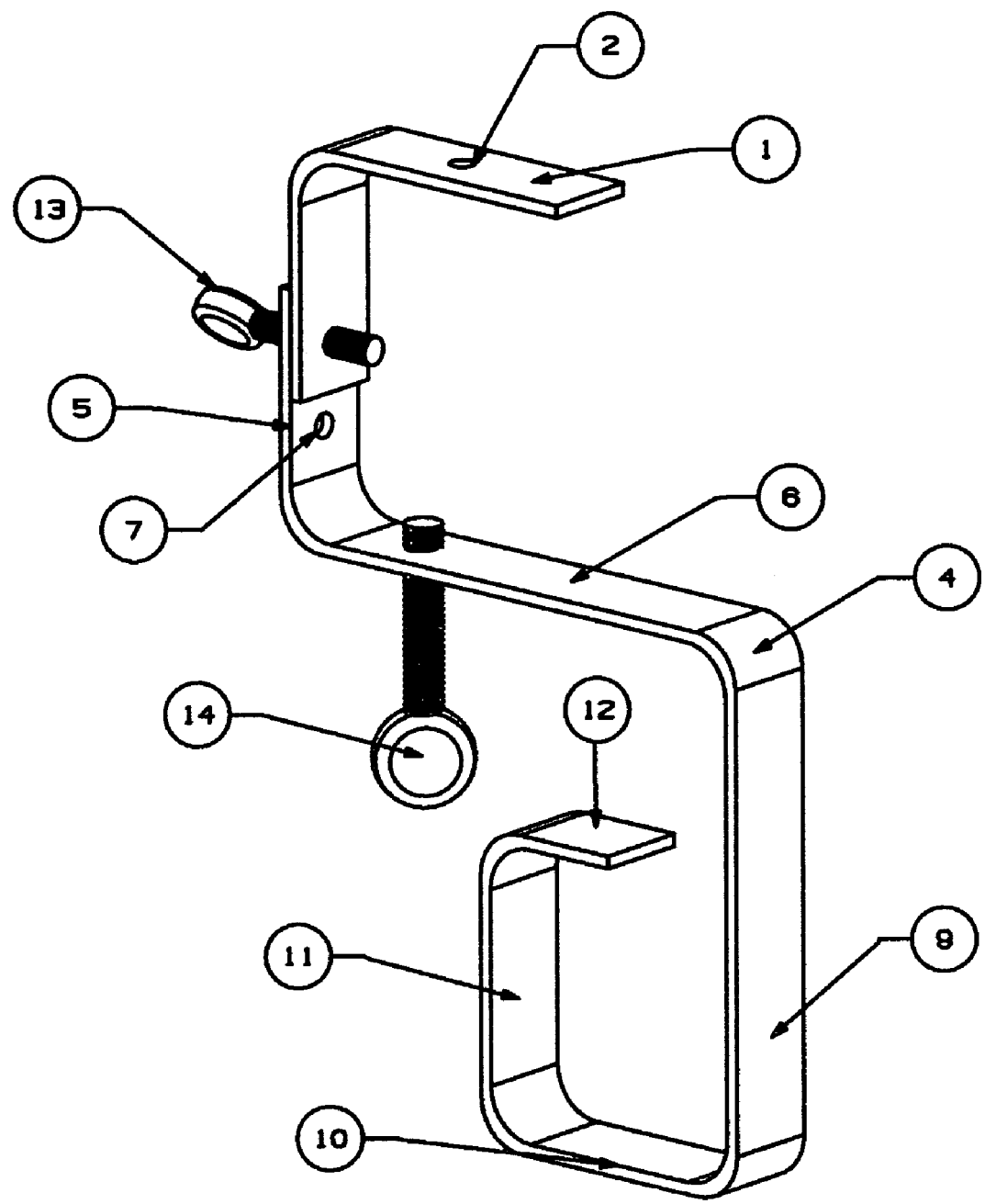
FIG. 3 shows the instant invention in perspective view.
Figure 4:
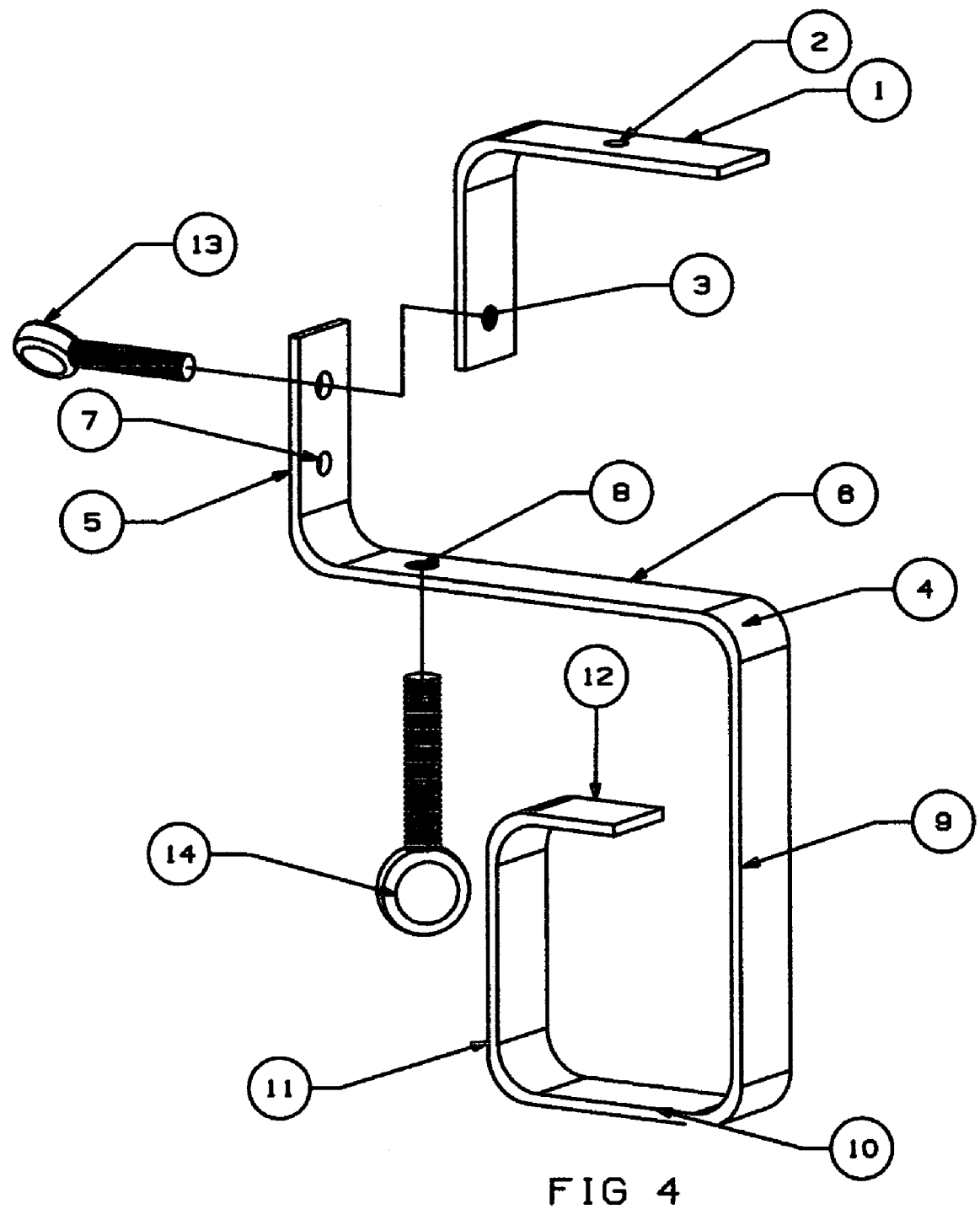
FIG. 4 is an exploded view of the instant invention.
Figure 5:
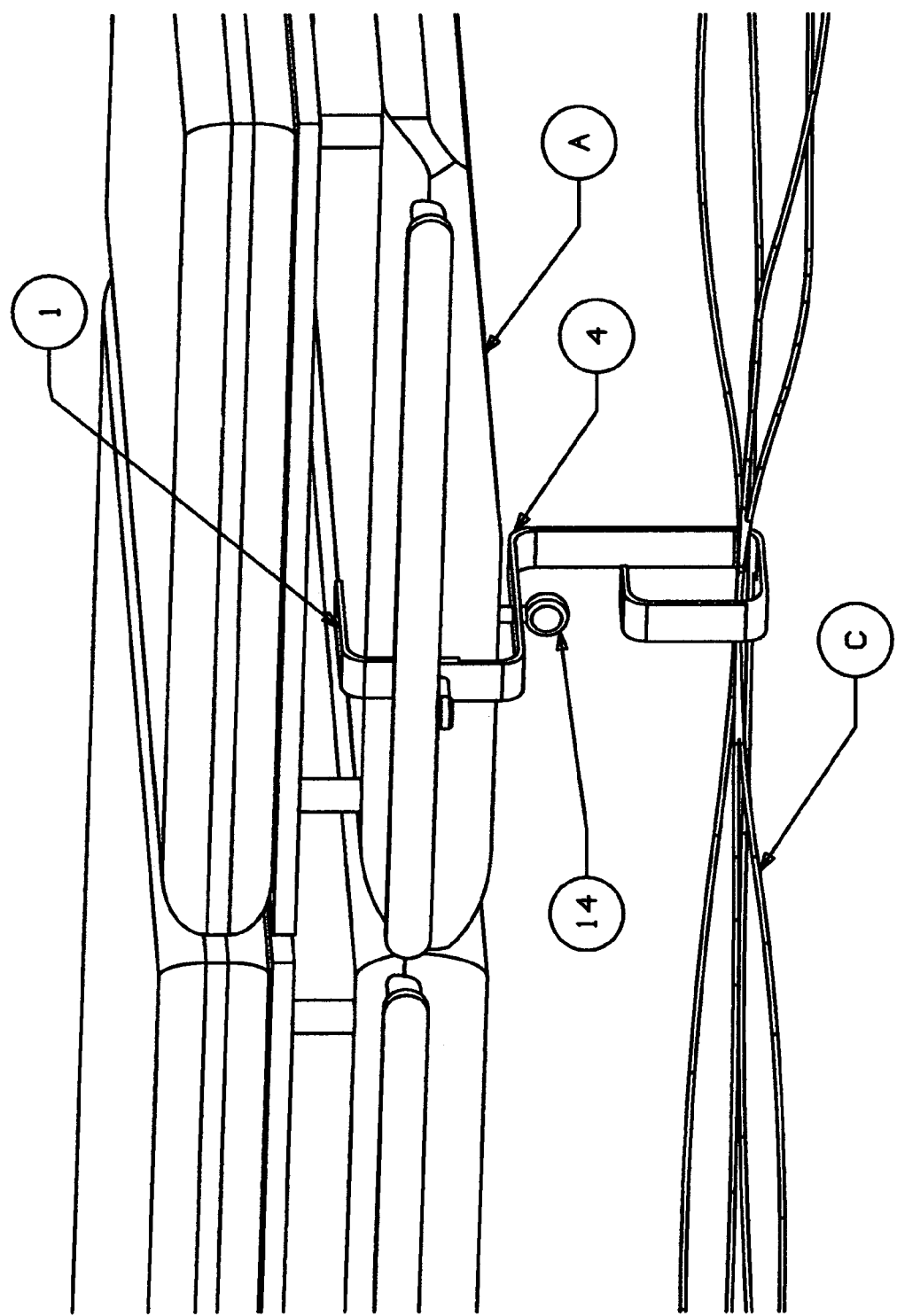
FIG. 5 is a close up view of the instant invention shown affixed to the table top of an operating room table.

FIG. 1 depicts a surgical operating table A attached to and about which there are surgical cords C emanating to and from surgical accessory units such as accessories B and D. FIG. 2 depicts what is seen in FIG. 1 except that various fully assembled surgical cord holders are seen affixed to the tabletop portion of table A and holding cords C off from the floor of the operating room where table A would be located and away from where the feet of a surgeon and his/her assistants would be found. FIG. 3 depicts the fully assembled surgical cord holder in perspective view. First connecting unit 1 thereof is in the shape of essentially a right angle. A through hole 2 is seen in the first leg thereof. A through hole 3 in the second leg thereof shown in FIG. 4 is shown receiving a first turning screw component 13. Second connecting unit 4 thereof is polysided. It consists of a first vertically inclined side 5 which bends gently at an end thereof into a first horizontally inclined side 6. A threaded through hole 7 in the first vertically inclined side threadably receives first turning screw component 13 after it would have first been inserted through hole 3. A threaded through hole 8 shown in FIG. 4 in first horizontally inclined side 6 threadably receives second turning screw component 14. First horizontally inclined side 6 bends gently at an end thereof and becomes second vertically inclined side 9 which in turn bonds gently at an end thereof to become second horizontally inclined side 10. Second horizontally inclined side 10 bends gently at an end thereof to become third vertically inclined side 11 which in turn bends gently at an end thereof to become third horizontally inclined side 12. Side 5 is shorter in length than side 11 and side 11 is in turn shorter in length than side 9. Also, side 12 is shorter in length than side 10 which in turn is shorter than side 6. Also, side 6 and side 10 are directed opposite one another. Side 12 is directed in the same direction as side 6. In view of the overall contours and design of second connecting piece 4, cords C can easily be held atop side 10 between sides 9 and 11 and beneath side 12 upon affixation of the cord holder to a table A as can readily be seen with resort to FIG. 5. The fully assembled surgical cord holder is affixed to the tabletop portion of a table A by way of first turning screw component 13 being inserted through either hole 2 or hole 3 threadably into and through hole 7 and being screwed fast against one of the lateral sides of the tabletop portion of table A and with second turning screw component 14 being threadably inserted into and through hole 8 and being screwed fast against the bottomside of the tabletop portion of table A. A screw cap 15 affixable to the end of turning screw component 13 serves to enhance fastening of the assembled surgical cord holder as against a lateral side of the tabletop portion of table A. A screw cap 15 likewise affixable to the end of turning screw component 14 serves to enhance fastening of the assembled surgical cord holder as against the bottomside of table A. For a second embodiment of the instant invention, the presence of a plurality of threaded through holes 7 in side 5 facilitates accommodation of affixation of the fully assembled invention to tabletop portions of surgical operating tables A that are of varying depths.

In conclusion, respectfully submitted, the instant invention is unquestionably new, useful and unique by virtue of the manner in which it serves to alleviate as efficaciously as it does, the omnipresent problem of wiring and cord clutter on the floors of contemporary operating rooms in today's hospitals to thereby greatly promote the goal of enhanced patient safety during surgery.

What is claimed is:

1. A two-piece surgical cord holder, comprising:
   a. a first connecting unit;
   b. said first connecting unit being in the shape of nearly a right angle;
   c. a first through hole through a first leg of said first connecting unit;
   d. a second through hole through a second leg of said first connecting unit;
   e. a first turning screw component;
   f. a second connecting unit;
   g. said second connecting unit being polysided and having initially a downwardly directed first vertically inclined side;
   h. said first vertically inclined side having a threaded through hole in it;
   i. said first vertically inclined side becoming, at a lower end thereof, a first horizontally inclined side;
   j. said first horizontally inclined side having a threaded through hole on it;
   k. a second turning screw component;
   l. said first turning screw component being insertable through one of said through holes in one of said legs of said first connecting unit and into and through said threaded through hole of said first vertically inclined side upon assembly of said first connecting unit to said second connecting unit and affixation of said assembled surgical cord holder to a tabletop portion of a surgical operating table;
   m. said second turning screw component being insertable into through said threaded through hole in said first horizontally inclined side upon affixation of said assembled surgical cord holder to said tabletop portion of said surgical operating table;
   n. said first horizontally inclined side becoming, at an outer end thereof, a downwardly directed second vertically inclined side longer in length than said first vertically inclined side;
   o. said second vertically inclined side becoming, at a lower end thereof, a second horizontally inclined side directed opposite to a direction of said first horizontally inclined side with said second horizontally inclined side being shorter in length than said first horizontally inclined side;
   p. said second horizontally inclined side becoming at an end thereof are upwardly directed third vertically inclined side shorter in length than said second vertically inclined side, and longer in length than said first vertically inclined side;
   q. said third vertically inclined side becoming at an upper end thereof a third horizontally inclined side directed in a same direction as said direction of said first horizontally inclined side and being shorter in length than said second horizontally inclined side, and;
   r. said fully assembled surgical cord holder being affixed to said tabletop portion of said surgical operating table by way of said first turning screw component being turned firmly into a lateral side of said tabletop portion of said surgical operating table with said second turning screw component being turned firmly into a bottom side of said tabletop portion of said surgical operating table.

2. A two-piece surgical cord holder, comprising:
   a. a first connecting unit;
   b. said first connecting unit being in the shape of nearly a right angle;
   c. a first through hole through a first leg of said first connecting unit;
   d. a second through hole through a second leg of said first connecting unit;
   e. a first turning screw component;
   f. a second connecting unit;
   g. said second connecting unit being polysided and having initially a downwardly directed first vertically inclined side;
   h. said first vertically inclined side having a plurality of threaded through holes in it;
   i. said first vertically inclined side becoming, at a lower end thereof a first horizontally inclined side;
   j. said first horizontally inclined side having a threaded through hole on it;
   k. a second turning screw component;
   l. said first turning screw component being insertable through one of said through holes in one of said legs of said first connecting unit and into and through any of said threaded through holes of said first vertically inclined side upon assembly of said first connecting unit to said second connecting unit and affixation of said assembled surgical cord holder to a tabletop portion of a surgical operating table;
   m. said second turning screw component being insertable into through said threaded through hole in said first horizontally inclined side upon affixation of said assembled surgical cord holder to said tabletop portion of said surgical operating table;
   n. said first horizontally inclined side becoming, at an outer end thereof, a downwardly directed second vertically inclined side longer in length than said first vertically inclined side;
   o. said second vertically inclined side becoming, at a lower end thereof, a second horizontally inclined side directed opposite to a direction of said first horizontally inclined side with said second horizontally inclined side being shorter in length than said first horizontally inclined side;
p. said second horizontally inclined side becoming at an end thereof are upwardly directed third vertically inclined side shorter in length than said second vertically inclined side, and longer in length than said first vertically inclined side;
q. said third vertically inclined side becoming at an upper end thereof a third horizontally inclined side directed in a same direction as said direction of said first horizontally inclined side and being shorter in length than said second horizontally inclined side, and;
r. said fully assembled surgical cord holder being affixed to said tabletop portion of said surgical operating table by way of said first turning screw component being turned firmly into a lateral side of said tabletop portion of said surgical operating table with said second turning screw component being turned firmly into a bottom side of said tabletop portion of said surgical operating table.

3. The two-piece surgical cord holder of claim 1, whereby, said first turning screw component is fitted with a screw cap.

4. The two-piece surgical cord holder of claim 2, whereby, said first turning screw component is fitted with a screw cap.

5. The two-piece surgical cord holder of claim 1, whereby, said second turning screw component is fitted with a screw cap.

6. The two-piece surgical cord holder of claim 2, whereby, said second turning screw component is fitted with a screw cap.

* * * * *